United States Patent [19]
Preves et al.

[11] Patent Number: 4,986,281
[45] Date of Patent: Jan. 22, 1991

[54] METHOD FOR OBTAINING A SIGNAL FOR ANALYZING HUMAN AND ANIMAL JOINT FUNCTIONS

[75] Inventors: David A. Preves, Edina; Brian P. Rosengren, Eden Prairie; James E. Holte, Minneapolis; Myer S. Leonard, Golden Valley, all of Minn.

[73] Assignee: Starkey Laboratories, Inc., Eden Prairie, Minn.

[21] Appl. No.: 469,756

[22] Filed: Jan. 12, 1990

Related U.S. Application Data

[63] Continuation of Ser. No. 643,848, Aug. 23, 1984, abandoned.

[51] Int. Cl.[5] .............................................. A61B 5/11
[52] U.S. Cl. .................................................... 128/782
[58] Field of Search ................... 178/660.01, 739, 773, 178/774, 782; 73/602, 641; 455/126, 158

[56] References Cited

U.S. PATENT DOCUMENTS

| Re. 29,008 | 10/1976 | Ott | 128/774 |
|---|---|---|---|
| 3,181,528 | 5/1965 | Brackin | 128/773 |
| 3,345,979 | 10/1967 | Miura et al. | 128/773 |
| 3,872,443 | 10/1976 | Ott | 128/774 |
| 3,934,204 | 1/1976 | Hill | 455/136 |
| 4,048,986 | 9/1977 | Ott | 128/653 |
| 4,220,160 | 9/1980 | Kimball et al. | 128/773 |
| 4,437,473 | 3/1984 | Mollan | 128/774 |

OTHER PUBLICATIONS

Ovellette, "Journal of the American Dental Association", vol. 89, Sep. 1974, pp. 623–628, copy in file.
Gibbs et al, "The Journal of Prosthetic Dentistry", vol. 46, No. 4, Oct. 1981, pp. 444–449, copy in file.
Chu et al, "Medical and Biological Engineering and Computing", vol. 16, No. 4, Jul. 1978, pp. 437–442, copy in file.
Conant, "Journal of Peridontology", vol. 33, 1962 pp. 322–327, copy in file.
Barrs, et al, "Archives of Otolaryngology", vol. 107, Jun. 1981, pp. 337–339, copy in file.
Maugh, II, "Science", vol. 214, Oct. 9, 1981, p. 172, copy in file.
Vogel, "Technology Illustrated", Dec. 81–Jan. 82, pp. 15–16, copy in file.

*Primary Examiner*—William E. Kamm
*Attorney, Agent, or Firm*—John W. Adams

[57] ABSTRACT

A non-invasive, non-ionizing, reproducible method and apparatus for analyzing the normal and abnormal function of human and animal joints is presented. The method includes passing vibrations through the joint to be analyzed and measuring the modulation of the amplitude and the phase characteristics of the vibrations caused by movement of the joint through a predetermined cycle. More specifically, the method includes transmitting a sinusoidal vibratory signal through a joint structure to be analyzed and measuring the amplitude and phase of the signal received on the opposite side of the joint during a prescribed movement of the joint both with and without the application of external mechanical forces, and comparing the profile of the modulated signal to the profiles obtained from reference joints. The apparatus includes a piezoelectric or magnetic transducer adapted to be positioned on one side of a joint to be analyzed to provide the vibrational signal and one or more receiving transducers placed on the other side of the joint to detect the modulated vibratory signal produced by the associated joint structure.

4 Claims, 2 Drawing Sheets

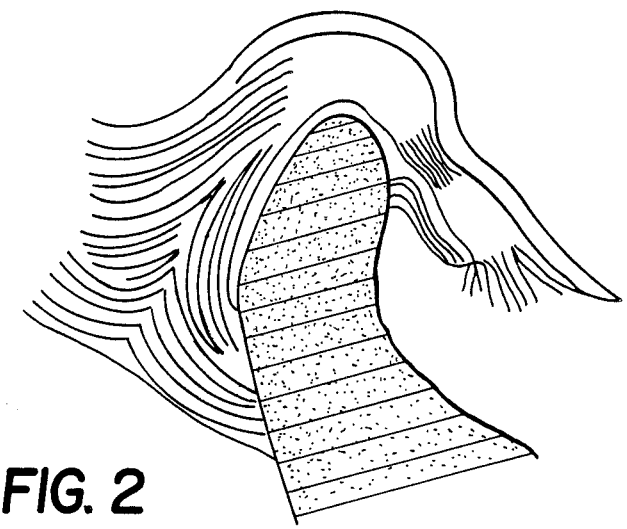
FIG. 2
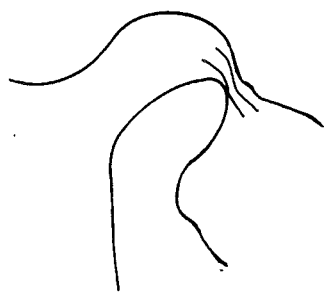
FIG. 3
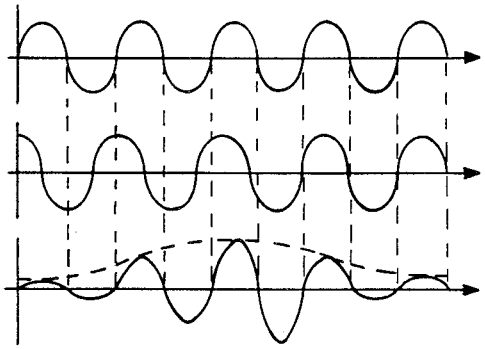
FIG. 5a
FIG. 5b
FIG. 5c
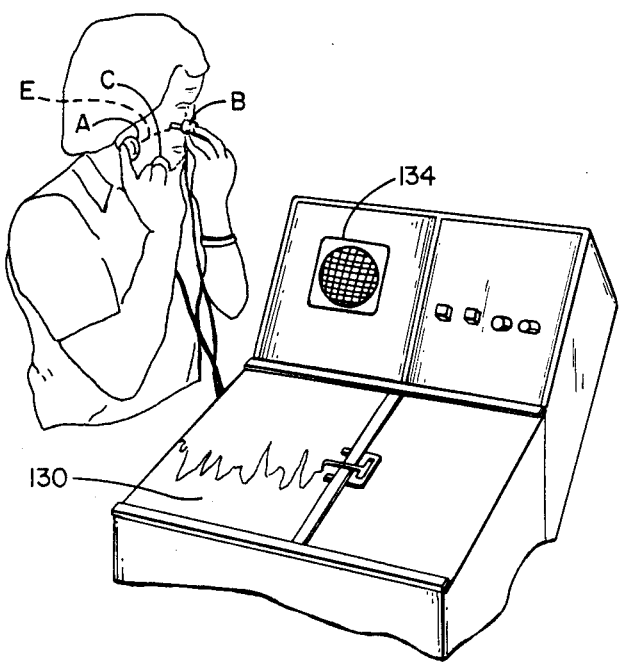
FIG. 1

METHOD FOR OBTAINING A SIGNAL FOR ANALYZING HUMAN AND ANIMAL JOINT FUNCTIONS

This is a continuation of application Ser. No. 643,848, filed Aug. 23, 1984 and now abandoned.

BACKGROUND OF THE INVENTION

In the past, various methods have been used for studying bones and joints. The closest prior art work appears to be that in which sound transmission through the teeth of a closed jaw was used to measure the occlusal force produced during chewing and swallowing. None of the prior art shows any method or apparatus for using the modulation of the amplitude and/or the phase of a sound signal as a means for studying bone and joint characteristics of a human or animal joint.

SUMMARY OF THE INVENTION

The method and apparatus embodying this invention is designed to determine the tissue and morphologic properties of human or other animal joint structures as these properties change in time due to a predetermined, programmed movement of the joint structure. This determination is obtained by studying the effects of resiliency, inertial and energy loss characteristics of the joint structure on an acoustic signal during articulation and/or stressing of that joint.

The method embodies passing a series of sinusoidal vibrations or a combination of sinusoidal vibrations through the joint to be analyzed and measuring the modulation of the amplitude and/or the phase of the vibrations caused by movement of the joint through a predetermined opening and closing and comparing the amplitude and/or phase modulations with the modulations characteristic of a reference joint function. These magnitude and phase measurements are carried out both with the joint moving freely, as well as with external mechanical forces applied to the joint. For example, hip and knee joints give different signatures when body weight is applied to the joint and when it is not.

The apparatus which has been found to be satisfactory includes an acoustical signal source designed to transmit sinusoidal vibrations having a frequency of approximately 1,200 Hz into a predetermined transmission location with respect to the joint to be studied. The signal is transmitted through the flexing joint structure and is picked up by a receiver, compared with the input signal to determine amplitude and/or phase modulations introduced by the flexing joint, and thereafter categorized with signal modulations obtained from a clinical population of normal and abnormal joints.

The apparatus includes a bone vibrator, a number of which are well known in the prior art, together with conventional receiving transducers which are combined with associated circuitry, as shown. The components of the electronic circuit subtract the output signal received through the joint from the input signal being transmitted into the joint to produce a resultant signal which represents the amplitude and phase of the signal transfer function of the joint being examined.

DESCRIPTION OF THE DRAWINGS

FIG. 1 is a perspective view of apparatus embodying the invention;

FIG. 2 is a diagrammatic view of the human temporomandibular joint with the mandible in the fully closed position (sagittal plane);

FIG. 3 is a similar view with the mandible in the open position;

FIGS. 5a, b, and c are a composite diagrammatic view showing exaggerated modulated signals of the phase and amplitude characteristics of the signal passed through a joint as compared with an input sine wave signal.

DETAILED DESCRIPTION OF A PREFERRED EMBODIMENT OF THE INVENTION

Figure 4:
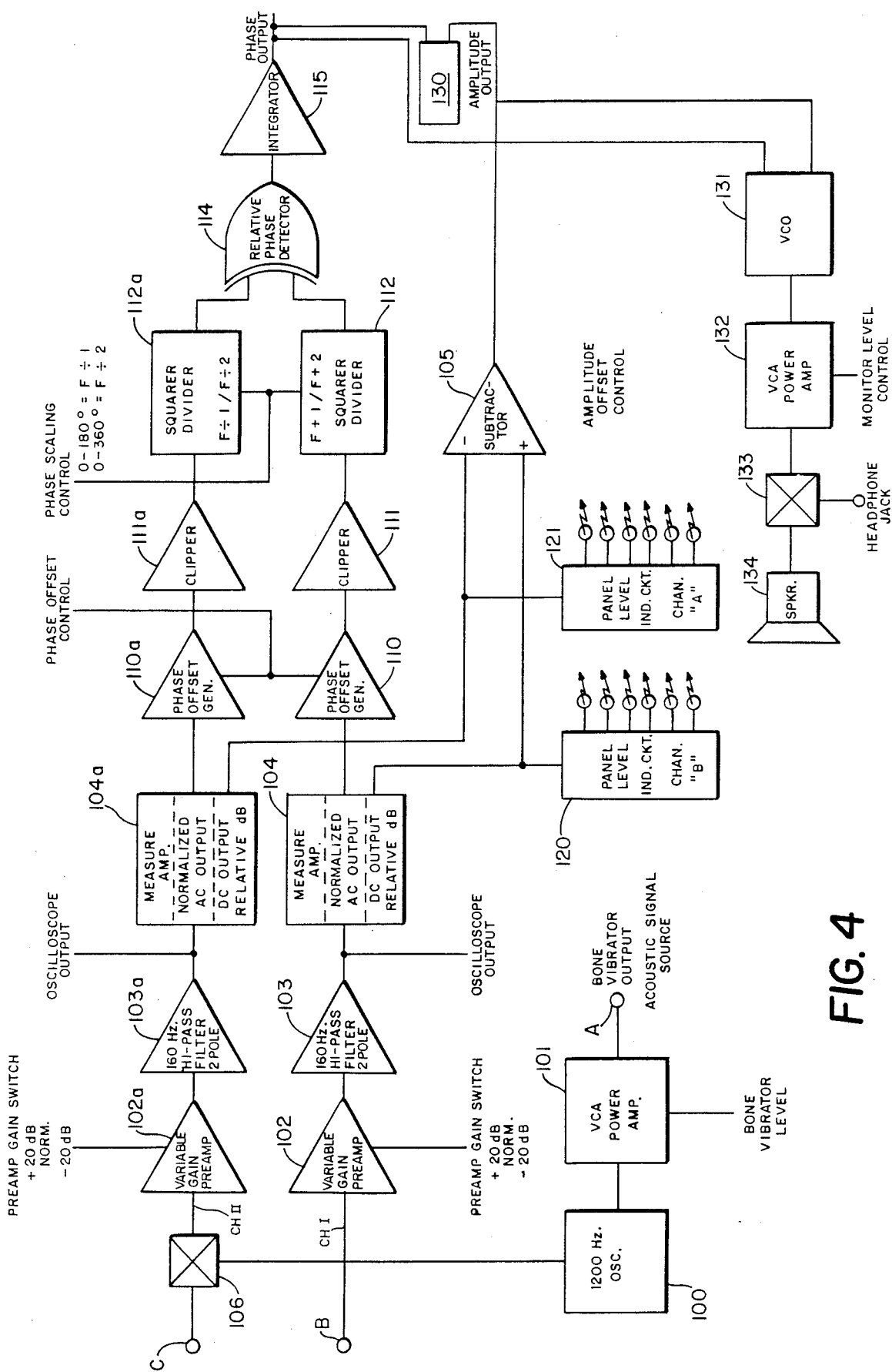
FIG. 4 is a circuit diagram of apparatus embodying the invention.

FIG. 1 shows the clinical configuration for the application of the instrument in a human temporomandibular joint analysis. In the form shown, two transducers, A and B, are illustrated. Transducer A serves as the source of the acoustic sinusoidal signal. Transducer B receives the acoustic signal. Transducers A and B are respectively positioned at predetermined landmarks on the two bones comprising the joint to be studied. The center line of primary pathway of the signal through the joint is illustrated by the dashed line E in FIG. 1.

The circuit diagram in FIG. 4 shows a signal-producing oscillator 100 which in the form shown, is designed to produce a sinusoidal signal of approximately 1200 Hz. The signal passes through a power amplifier component 101 to transmitter A. As shown in FIG. 1, transmitter A is placed on the corner of the jaw (at the angle of the mandible) and transducer B is located on the cheekbone (at the zygomatic arch) as shown. The acoustic signal is transmitted through the bone and associated soft tissues of the joint. The signal received by transducer B (as modulated by the joint structure) is fed through series of components designated as Channel I which includes a variable gain preamplifier 102 followed by a high pass filter 103 to minimize any power line interference. The filtered signal is then input to a measure amplifier 104 which is a combination of a logarithmic amplifier and automatic gain control loop which divides the signal into two separate outputs; one is a normalized AC output of a given level regardless of input level, and other is the envelope of the joint modulation imposed on the 1200 Hz input signal picked up by transducer B.

A second channel may be provided such as Channel II which includes circuitry similar to the Channel I circuit just described. Channel II is provided to process either the signal produced by the oscillator 100 as shown in the diagram in FIG. 4 or to provide a comparison modulation signal, either of which may be input to the subtractor 105. The circuitry of Channel II includes a variable gain preamplifier 102a, a high pass filter 103a and a measure amplifier 104a which are respectively similar to the corresponding components previously described for Channel I. A switch 106 controls the input to Channel II and permits the operator to select a comparison signal that is input to a subtractor 105, which subtracts the signal delivered from measure amplifier 104a from the modulated signal 104 to produce an amplitude output which represents the amplitude modulation imposed by the joint structure on the 1200 Hz input signal. This configuration allows the modulated signal received by transducer B to be compared either with the output from oscillation 100 or with another modulation signal produced by a second receiver C positioned at a second receiving location which is selected to emphasize certain desired characteristics of the joint transmission.

It will be apparent from FIG. 1 that sending transducer A produces a sound path directly through the mandible jaw bone section to the receiving transducer C and that this signal can then be compared to the signal through the mandible joint to the receiving transducer B, as indicated in the block circuit diagram (FIG. 4). Any modulation produced by variations in the contact between driver A and the jaw will be present int he signal received at B as well as at C and therefore, can be cancelled out when the two signals at B and C are differenced. This results in a signal which reflects only the modulation produced by the joint. Since the solid bone structure does not produce modulation of the signal, the two signals received at B and C will be affected similarly, thus resulting in a signal which reflects only the modulation produced by the joint structure.

The determination of the phase of the received signal relative to the transmitted signal may also be accomplished with the circuitry illustrated in FIG. 4. Such determination of phase modulation presents characteristics of the joint structure that in some cases are more important than the amplitude modulation determination described earlier.

The normalized AC outputs from the measure amplifiers 104 and 104a pass through phase offset generators 110 and 110a which allow for the introduction of a variable phase calibration signal. Clippers 111 and 111a preserve the zero crossing information associated with the two channels. The squarer-divider circuits 112 and 112a together with the relative phase detector 114 and integrator 115 produce a signal proportional to the phase difference between the signals input to Channel I and Channel II biased by any offset introduced at generators 110 and 110a. This detection is accomplished by using the integrator to convert the pulse-width voltage from the relative phase detector 114 into a voltage which represents the modulation of the phase of the input signal from transducer A produced by the opening and closing of the joint as received by transducer C. Panel level indicator lights are provided for Channels I and II by light panels 120 and 121 shown in FIG. 4.

The modulated amplitude signal from subtractor 105 may be recorded on any conventional X-Y strip recorder 130, such as is manufactured by Bruel & Kjaer, Model 2307, manufactured in Denmark, and may also be delivered to a voltage controlled oscillator 131, a voltage controlled power amplifier 132, and to a head phone set 133 and/or a speaker 134 as shown in FIG. 4 to permit the operator to listen to the received modulated signal from either Channel I or Channel II.

Similarly, the phase output signal from integrator 115 may be delivered to the conventional X-Y recorder 130 or to the head phones 133 and speaker 134 through the VCO 131 and VCA 132.

FIGS. 5a, b and c respectively illustrate diagrammatically an input signal, and exaggerated modulated signals representing the phase and amplitude characteristic signals compared at corresponding time reference points through 4½ cycles. FIG. 5b shows an exaggerated phase characteristic output signal and depicts the phase modulation of the input signal produced by the joint structure being studied. FIG. 5c depicts an exaggerated amplitude characteristic output signal as modulated by a joint structure being studied. The dotted line in FIG. 5c represents the envelope of the modulated amplitude characteristic signal illustrated. Variations in these modulated signals will permit the clinician to determine the structural characteristics of the bone and tissue structures of the joint being studied and facilitate diagnosis of irregularities in the joint.

It will be seen that this invention provides method and apparatus for analyzing human and animal joint function to provide diagnostic assistance of the bone and tissue joint structure.

What is claimed is:

1. A non-invasive method for obtaining a signal to be used for analyzing functions of human and animal joints which comprises:
    producing a sinusoidal vibrational first signal having a signal predetermined frequency with measurable phase and amplitude characteristics,
    transmitting the first signal through the joint to be analyzed,
    moving the joint through a series of positions during such transmission to produce a modulated signal,
    detecting at least one of the characteristics of the modulated signal after the transmitted signal has passed through the joint during opening and closing thereof,
    presenting for analysis the detected modulated signal,
    and detecting the transmitted signal without passing the same through the articulated joint and differencing the second detected signal from the first detected signal to produce a resultant signal modulated solely by the transmission of the signal through the articulated joint.

2. The method set forth in claim 1 wherein the characteristic of the modulated signal being detected constitutes the amplitude characteristic of the signal passing through the joint.

3. The method set forth in claim 1 wherein the characteristic of the modulated signal being detected constitutes the phase characteristic of the signal passing through the joint.

4. The method set forth in claim 1 wherein the characteristic of the modulated signal being detected constitutes both the phase and amplitude characteristic of the signal passing through the joint.

* * * * *